United States Patent [19]
Downey et al.

[11] Patent Number: 6,149,578
[45] Date of Patent: Nov. 21, 2000

[54] PISTON-ACTION INTRA-AORTIC CORONARY ASSIST DEVICE

[75] Inventors: H. Fred Downey; Xiaoming Bian, both of Fort Worth, Tex.

[73] Assignee: My-Tech, Inc., Tampa, Fla.

[21] Appl. No.: 09/244,906

[22] Filed: Feb. 4, 1999

[51] Int. Cl.[7] .................................................. A61M 1/12
[52] U.S. Cl. .............................................................. 600/18
[58] Field of Search ............................................... 600/18

[56] References Cited

U.S. PATENT DOCUMENTS

| | | | |
|---|---|---|---|
| 4,531,936 | 7/1985 | Gordon | 604/49 |
| 4,697,574 | 10/1987 | Karcher et al. | 128/1 D |
| 4,741,328 | 5/1988 | Gabbay | 600/18 |
| 4,771,765 | 9/1988 | Choy et al. | 600/18 |
| 4,785,795 | 11/1988 | Singh | 600/18 |
| 4,804,358 | 2/1989 | Karcher et al. | 600/17 |
| 4,861,330 | 8/1989 | Voss | 600/18 |
| 5,195,942 | 3/1993 | Weil et al. | 600/18 |
| 5,395,353 | 3/1995 | Scribner | 604/264 |
| 5,484,412 | 1/1996 | Pierpont | 604/101 |

Primary Examiner—William E. Kamm
Attorney, Agent, or Firm—Charles D. Gunter, Jr.

[57] ABSTRACT

An intra-aortic balloon assist device is used to increase blood flow to the coronary arteries of an injured heart. The device comprises an expandable member that is placed within the ascending aorta of the patient, coupled to a flexible tube made of standard catheter material. The flexible tube is coupled to a blood flow control means within the descending portion of the patient's aorta. When operating, the blood flow control means pumps a surge of oxygenated blood through the flexible tube and expandable member into the area around the ascending portion of the aorta. The expandable member is operated in successive stages. The first stage is a collapsed stage, which is a completely depressurized stage of the member. In the second, blocking stage, the member blocks off the aorta to create a closed volume around the ascending portion of the aorta. In the third, blocking-pumping stage, the member expands in the direction of the coronary arteries simultaneous to the surge of blood supplied by the blood flow control means to force oxygenated blood within the closed volume—blood supplied by the blood flow control means and blood already within the closed volume—towards the coronary ostiums.

19 Claims, 3 Drawing Sheets

PISTON-ACTION INTRA-AORTIC CORONARY ASSIST DEVICE

BACKGROUND OF THE INVENTION

1. Field of the Invention

The present invention relates in general to a device and method for coronary perfusion, and in particular to an intra-aortic coronary perfusion device. Still more particularly, the present invention relates to a piston-action balloon device which creates a high blood pressure region in the ascending aorta for the purpose of simultaneously perfusing the left and right coronary arteries in an injured or diseased patient's heart.

2. Description of the Prior Art

Heart disease is the leading cause of death in the United States and Europe. It is estimated that one in five individuals over the age of 60 will die of a heart attack resulting from heart disease in the United States. The primary cause of heart attacks are inadequate coronary blood supply, an anatomical disorder, or conduction disturbances. The particular cause of heart attacks and heart failures, and the damage that ensues, is the result of ischemic injury.

A tissue is ischemic when it receives an inadequate supply of oxygen because of inadequate blood flow. The most common cause of ischemic injury to the heart, or myocardial ischemia, is atherosclerosis of the coronary arteries. This is an occlusion of the arteries that supply the heart muscle, the coronary arteries, with oxygenated blood. The result of this blockage is a loss of blood flow to the heart muscle, thus a lack of oxygen to these tissues. Another major cause of ischemic injury is operative procedures on the heart, during which blood flow may be diverted or occluded from at least a portion of the cardiac tissue. Myocardial cells (heart tissue cells) are adapted to respire aerobically and cannot respire anaerobically for more than a few minutes. If ischemia and anaerobic respiration continues for more than a few minutes, necrosis (cellular death) will occur in areas of the heart where oxygen is most lacking. Thus, treatment of myocardial ischemia is critically time dependent.

There are a number of devices that are designed to treat blocked coronary arteries. Many of the devices to date share a common feature in that they are directed towards placement of a perfusion tube into either the left or right coronary artery, thus perfusing a particular coronary artery with oxygenated blood. These devices include the Karcher et al. (U.S. Pat. No. 4,804,358) device, which places a perfusion tube downstream from an occlusion in a coronary artery and uses an external oxygenated blood supply, the Scribner (U.S. Pat. No. 5,395,353) device, which is directed to a catheter that can be guided within the aorta into a particular coronary artery, then being placed near the ostium of the coronary artery, and the Pierpont (U.S. Pat. No. 5,484,412) device, which is several inflatable balloons acting to anchor a perfusion tube, while another balloon is used in an angioplasty procedure, being placed at the occlusion within a particular coronary artery. These devices are advantageous in directing an extra surge of oxygenated blood to where it is most needed—ischemically injured myocardium. However, these devices have the disadvantage of being difficult to use. Valuable time and expertise is necessary to determine which coronary artery to perfuse. Still more time is lost in inserting the device into the aorta and locating the ostium of the coronary artery. Further, these devices also incorporate extra-corporeal blood pumps that require an external source of blood, adding to the undesirability of these devices.

Ischemic injury can also occur to the cardiac tissue after surgery is performed on the heart and after procedures are performed on the coronary circulation to restore coronary blood flow. Surgical procedures on the heart often deplete the cardiac tissues of oxygen or produce other damage, which can result in prolonged depression of contractile function (stunned myocardium), even if not in fully developed ischemic injury to the myocardium. Procedures to restore coronary blood flow by thrombolysis or agioplasty can produce re-perfusion injury, which also results in stunned myocardium. Stunned myocardium gradually recovers normal contractile function if coronary blood flow can be maintained. As a result of myocardial stunning, the blood pressure can be diminished, thus resulting in loss of blood flow through the coronary arteries. As a result, the blood pressure can be diminished, thus resulting in loss of blood flow through the coronary arteries. This exacerbates recovery of the myocardium and can lead to more damage to the heart tissue. Post-operative measures are often taken to improve coronary artery blood pressure, thus normalizing heart function and improving the patient's overall blood pressure. The most common method used to improve the blood pressure post-operatively is a heart-lung machine. However, a heart-lung machine is limited in its usefulness due to the mechanical stresses placed on the blood elements. Anticoagulants such as heparin must be used in large quantities to inhibit blood clotting, but this can also lead to detrimental side effects such as excessive bleeding of the patient. When blood pressure is diminished following procedures to restore coronary blood flow, drugs can be administered to elevate the blood pressure, but this produces an additional burden on the heart.

Several devices have been designed to treat ischemic heart injury by placing a pumping balloon into the ascending portion of the aorta near the left and right coronary artery ostiums. Karcher et al. (U.S. Pat. No. 4,697,574) disclose a device that includes a propulsion balloon and a obturation balloon. The obturation balloon is placed upstream from the left subclavian artery, left common carotid artery, and brachiocephalic trunk to block the flow of blood during diastole. The propulsion balloon is placed in the space created by the obturation balloon and the heart valves, and is a simple rounded balloon designed to be inflated during diastole, decreasing the volume within the ascending artery and thus forcing oxygenated blood into the coronary arteries. The Singh (U.S. Pat. No. 4,785,795) invention is a modification of the Karcher et al. (U.S. Pat. No. 4,697,574) device, the Singh invention having an elongated balloon that can be used at a higher pumping frequency. Finally, there is a balloon device called SUPERCOR™ (ABIOMED™, Inc.) used to displace blood in the ascending aorta and thus, improve coronary diastolic blood flow.

Although an improvement on the prior state of the art, the Singh and Karcher et al. devices are limited to applying pressure upon the blood already within the space created by the blocking balloon and the heart valves. The present invention is an improvement on the prior art in that it incorporates the advantages of supplying an extra pulse of oxygenated blood to the coronary arteries through a blood flow control means, while closing off the blood flow from the ascending aorta and creating a high pressure region in the ascending aorta.

SUMMARY OF THE INVENTION

It is therefore one object of the present invention to provide a device and a temporary means for improving the flow of oxygenated blood to the coronary arteries of an injured or diseased heart.

It is another object of the present invention to block diastolic flow of blood from the ascending aorta into the aortic arch and descending aorta and to pump blood into the area surrounding the coronary ostiums.

It is another object of the present invention to provide a balloon-acting pump that has a piston action within the ascending portion of the aorta.

It is another object of the present invention to replace the need for a heart-lung machine after heart surgery, thus avoiding the detrimental effects of the machine and anticoagulants used with the machine.

It is another object of the present invention to increase coronary blood pressure after surgical procedures performed on the heart or coronary circulation.

It is another object of the present invention to provide a balloon-acting pump that has the dual purpose of plugging the aorta during diastole and pumping blood into the coronary arteries.

It is another object of the present invention to provide a balloon-acting pump that allows an extra surge of oxygenated blood to be pumped through the center of the balloon.

It is another object of the present invention to provide an surge of oxygenated blood from a blood flow control means such as a pumping balloon into the ascending aorta during diastole and simultaneously forcing the extra pulse of blood into the left and right coronary arteries by using a piston-acting pump balloon.

It is another object of the present invention to provide emergency medical practitioners with a simple to use intra-aortic device that can be used without specialized skill and greatly reduces the time to effect treatment of the injured or diseased heart.

The objects and features of the invention are achieved by providing a blood flow control means and a expandable member coupled by a flexible tube. The purpose of the blood flow control means is to alternately increase and decrease the blood pressure within an ascending aorta in synchrony with heart function. The blood flow control means is a pumping balloon that is located within a catheter-body, the catheter-body connected to an expandable member by a flexible tube having an inner bore, the member being located in the ascending aorta near the coronary ostiums. The pumping balloon and the catheter-body can be a device such as the Downey et al. (Ser. No. 09/082,559, now U.S. Pat. No. 5,891,012 and assigned to assignee of present invention) invention.

A flexible tube is provided having a proximal end and a distal end, the distal end being associated with the catheter-body and the proximal end being associated with the expandable member. The expandable member is a piston-action balloon that is actuable between a collapsed position, a blocking position and a blocking-pumping position. There is an opening at the proximal end of the tube to allow a surge of blood to flow from the pumping balloon to the ascending aorta. The expandable member is inflatable to the blocking and blocking-pumping positions to fit against the inside wall of an aorta in order to block blood flow during diastole. The expandable member in the blocking-pumping position extends distally to expand within an aorta, thus acting in a piston-like fashion, increasing the blood pressure upstream from the expandable member in synchrony with the surge of blood from the pumping balloon.

The flexible tube, expandable member, and catheter-body are placed within the aorta of a patient, the expandable member being positioned at a selected location within the ascending portion of the aorta of the patient. The mode of operation of the invention is as follows: starting from its collapsed position, the expandable member is inflated to the blocking position during diastole to block the downstream flow of blood in the ascending aorta. Next, the expandable member is further inflated to the blocking-pumping position during diastole in synchrony with an increase in blood pressure, the increase in pressure created by the surge of blood provided by the pumping balloon in its pumping position pumping blood through the flexible tube, thus forcing blood into the coronary arteries. Finally, the expandable member is deflated to its collapsed position during systole, allowing blood ejected from the left ventricle to flow downstream in the aorta. At the same time, the pumping balloon is deflated to draw blood from the ascending aorta through the flexible tube and into the catheter space around the pumping balloon. Then, the cycle is repeated.

Additional objects, features and advantages will be apparent in the written description which follows.

DESCRIPTION OF THE INVENTION

General Description of Device and its Position in Patient

Figure 1:
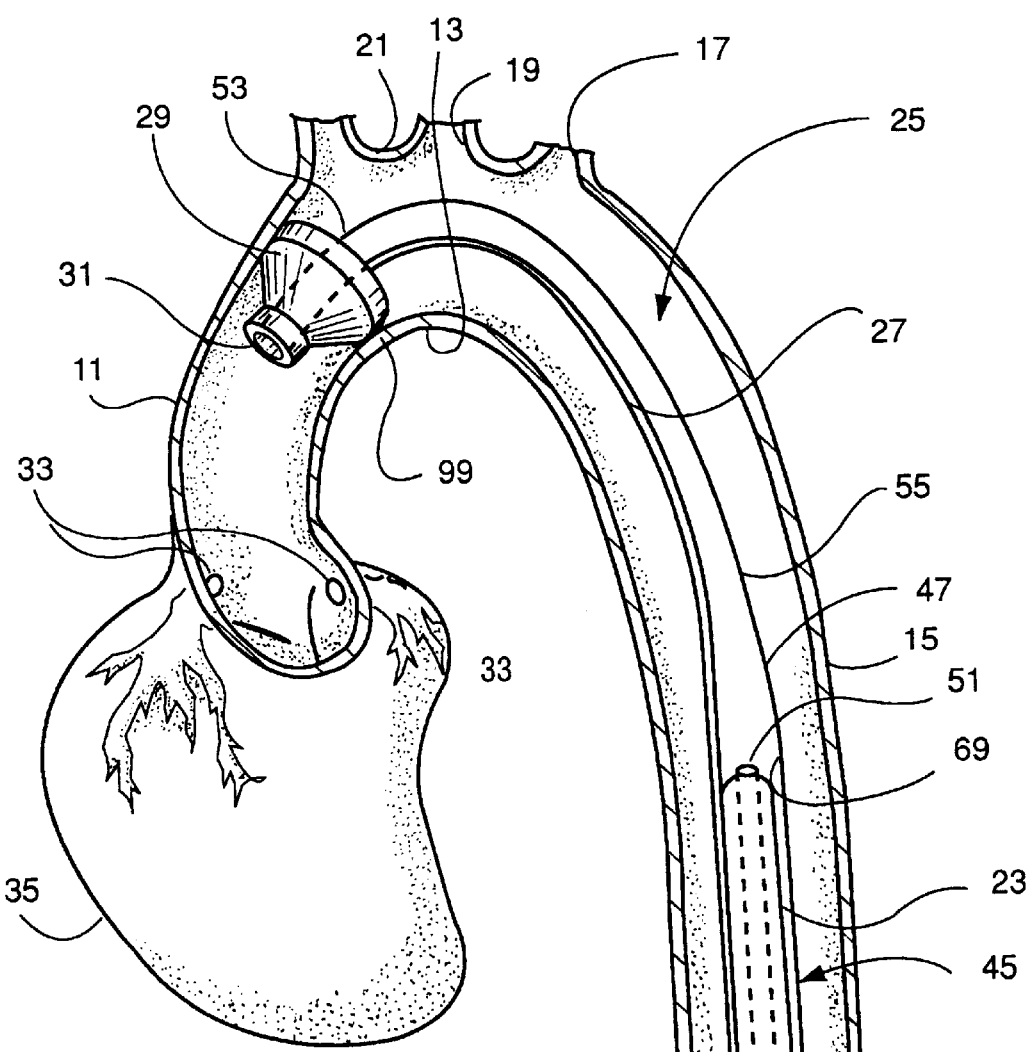
FIG. 1 is a cutaway view of the intra-aortic balloon assist device placed within the aorta.
Figure 1:
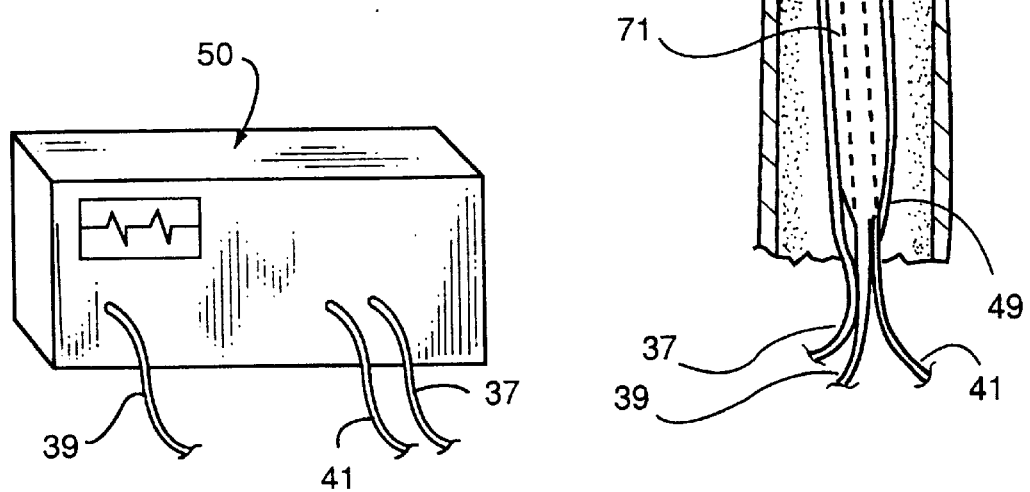

FIG. 1 is a simplified, isolated cut-away view of a human aorta, showing an embodiment of the present invention placed within the aorta. The invention is placed up through the descending aorta 15, through the aortic arch 13, and into the ascending aorta 11. At the aortic arch 13 are the three aortic arch arteries: the brachiocephalic trunk 21, the left common carotid artery 19, and the left subclavian artery 17. The heart 35 and left and right coronary ostiums 33 are located within the ascending aorta, the ostiums being near the placement of the expandable member 29 of the invention.

The present invention described in FIGS. 1, 2 and 3, and the alternative embodiment described below, is designed to temporarily assist human heart function in injured or diseased myocardium for several hours to several days. The invention is particularly useful in increasing the coronary blood flow after surgical procedures to the heart or in other conditions where aortic pressure is not sufficient for adequate coronary blood flow. The wall of the heart, or myocardium, is supplied with oxygen by the right and left coronary arteries. These two vessels are perfused with oxygenated blood at the ostiums 33 located at the base of the ascending part of the aorta 11. Thus, the heart supplies its own tissue with oxygen through oxygenated blood coming from the left ventricle. The coronary arteries encircle the heart within depressions on the surface of the heart. Due to the great oxygen demand of the rapidly metabolizing myocardium, an efficient and constant oxygen supply is vital. Disease, injury, or surgical procedures can cause a reduction of blood pressure which in turn reduces blood flow through the coronary arteries. The present invention is directed towards improving the function of the heart by increasing the diastolic blood pressure at the coronary ostiums.

FIG. 1 shows the placement of the invention in the aorta of a patient. The flexible tube 25 of the invention is typically placed within the descending aorta and aortic arch. The flexible tube 25 has an internal bore, a proximal end 53 and a distal end 55. The distal end is associated with the blood flow control means, and the proximal end is associated with the expandable member 29.

A blood flow control means must be provided. In general, reference to a blood flow control means is not limited to any particular type of device. The preferred means would be a device located within a rigid body in the aorta. This type of device would be located downstream from the coronary arteries. In the present invention, the blood flow control device is activated in two stages: a pumping stage or position and a sucking stage or position. The pumping stage increases blood pressure upstream from the device's location, while the sucking position decreases blood pressure upstream from the device's position. The blood flow control means must supply a surge of oxygenated blood in synchrony with the heart's normal rhythm. During diastole, the walls of the heart normally relax to allow blood to enter the left ventricle from the left atrium, containing oxygenated blood from the lungs. At this stage, the blood flow control means supplies a surge of oxygenated blood which supplements the function of the expandable member in order to pump blood into the coronary arteries. During systole, the walls of the left ventricle contract, pushing oxygenated blood from the left ventricle into the ascending aorta. At this stage, the blood flow control means would be in a sucking state, drawing blood from the ascending aorta.

In the embodiment of the invention shown in FIG. 1, a pumping balloon 23 placed within a catheter-body 45 is the blood flow control means. Although FIG. 1 describes one embodiment of the blood flow control means, the means can be a device as disclosed in Downey et al. (Ser. No. 09/082,559, now U.S. Pat. No. 5,891,012, presently pending and assigned to assignee of present invention), which is typically placed within the descending portion of the patient's aorta. The part of that device that otherwise would have been placed at a coronary artery has been replaced by the expandable member 29 and the port 31 for infusing blood into the aorta instead of directly into the coronary artery.

In the present embodiment in FIG. 1, the pumping balloon 23 is contained within catheter-body 45, the body having a proximal end 47 and distal end 49, and an outside wall 67 and an inside wall 69 forming a chamber. The pumping balloon in its pressurized, pumping position fills the chamber and makes uniform contact with inside wall 69, and in the sucking position creates the chamber where blood fills in around the depressurized balloon 23. The catheter-body 45 allows blood to flow past the external wall 67 within the descending portion of the aorta.

The pumping balloon is controlled by gas pressure supplied through tube 39, the pumping balloon having a sucking position when depressurized with gas, and a pumping position when pressurized with gas. A lumen 27 runs continuously through body 45, through flexible tube 25, being coupled to the expandable member 29. The lumen carries pressurizing gas to the member 29 from tube 37. Also, running longitudinally through the pumping balloon 23 is a pressure sensing tube 71 (shown in dashed lines in FIG. 1) ending in port 51. The pressure sensing tube ends in tube 41, tube 41 being coupled to an external pressure sensing device.

Function of Device

Figure 2:
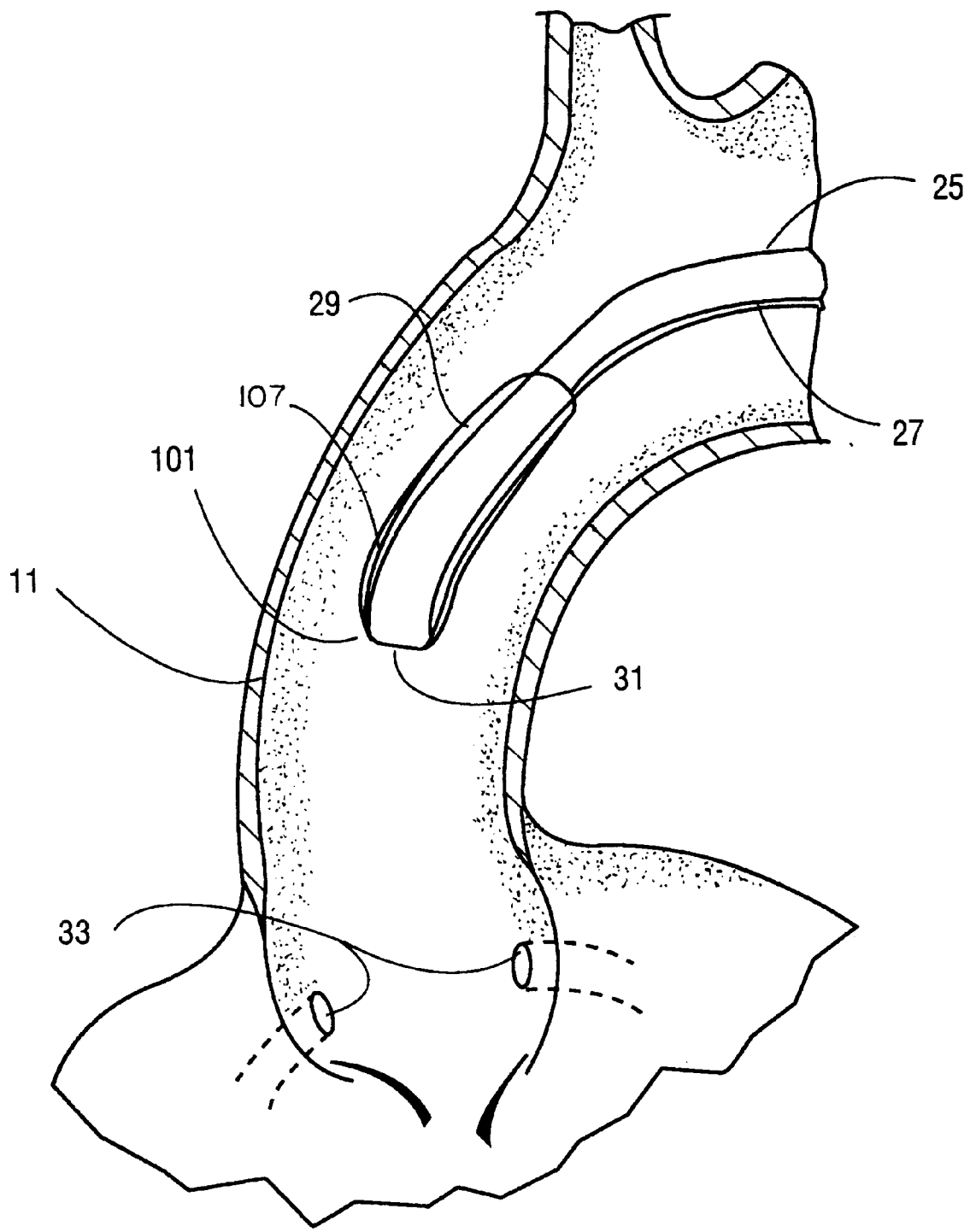
FIG. 2 is a close-up cutaway view of the piston action expandable member in its collapsed position.
Figure 3:
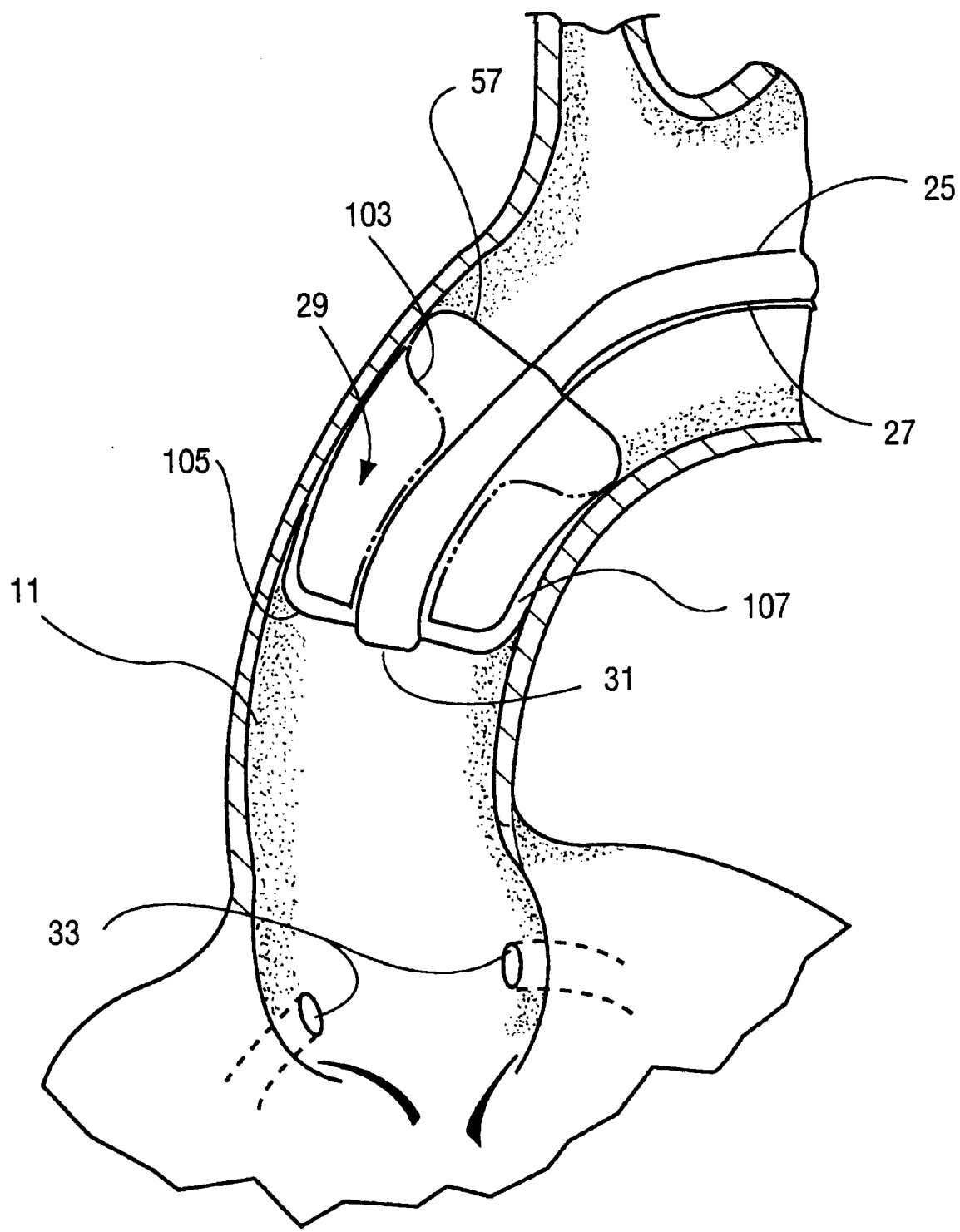
FIG. 3 is a close-up cutaway view of the piston action expandable member in its blocking (dashed line) and blocking-pumping (solid line) positions.

FIGS. 2 and 3 show how the expandable member operates in one embodiment of the invention. Once in place, the device is pressurized and depressurized with a gas to force blood into coronary arteries. This is accomplished by the cooperative pressurization and depressurization of the pumping balloon and the expandable member. First, the expandable member 29 is placed at the ascending portion 11 of the aorta above ostiums 33. The expandable member has three positions: the collapsed position, the blocking position, and the blocking-pumping position. The collapsed position 101 shown in FIG. 2, occurs when the expandable member 29 is depressurized, the flexible member material being drawn against the outside wall of the flexible tube's proximal end 53. Simultaneous to member 29 being in the collapsed position, pumping balloon 23 is in its deflated sucking position. This is achieved by drawing gas from the pumping balloon to deflate the balloon material around the pressure sensing tube 71. This cooperative action is timed to take place during systole of the heart to help draw blood from the ascending aorta into the catheter-body, filling the chamber within the body 45 around the deflated balloon 23.

The next position of the member shown in FIG. 3 is the blocking position 103 (dashed lines), and occurs when the expandable member is inflated to a primary volume. In the blocking position, the expandable member 29 makes uniform and firm contact with the inside wall of the aorta at a circumferential portion 99. This has the effect of blocking the downstream flow of blood in the ascending aorta during the diastole phase of cardiac function. Thus, a closed volume is created between the outflow valve of the ventricle and the expandable member.

At the same time, the pumping balloon pumps blood through the flexible the internal bore of tube 25 and out opening 31. The pumping balloon works by being inflated with gas pressure, the pumping balloon being inflated against the inside wall 69 of the catheter-body, thus displacing the oxygenated blood within the catheter-body 45. Simultaneous to the surge of blood through opening 31 provided by balloon 23, the expandable member 29 is pressurized to a secondary volume, expanding in a direction distal to the flexible tube towards the heart 35 and ostiums 33. This position of the expandable member constitutes the blocking-pumping position 105 shown in FIG. 3, wherein the cycle of collapsed position, blocking position, and blocking-pumping position is repeated in synchrony with the pumping balloon.

Surrounding flexible tube 25 is a lumen layer 27 which is continuous with the length of the flexible tube. The lumen carries the gas, preferably helium, that is either pumped into or out of the expandable member 29. The lumen is continuous with the flexible tube, being ultimately attached to a tube 37 located outside the body to a gas control apparatus. The pressure of gas within the lumen to the expandable member is synchronized with the pulse of blood generated from the blood flow control means. By changing the gas pressure, the expandable member is brought into one of the three stages, 101, 103, or 105.

The blood pressure within the aorta is measured using pressure sensor port 51, which is at the terminal end of pressure tube 71 running the length of the pumping balloon exiting the catheter body into tube 41. An electrocardiogram can be used to control the external gas control apparatus, the gas control apparatus 50 in turn regulating the pressurization of the expandable member and pumping balloon. The gas control apparatus is coupled to the tubes 37 and 39. Operation of the system will be monitored by measuring the ascending aortic pressure from the pressure sensing port 51, which extends out of the patient at 41. The pressure sensor port 41 can also serve as an injection port, allowing the practitioner to inject substances into the ascending aorta for effective delivery into the coronary circulation and thus to assist in treating the patient.

Embodiments of Expandable Member

The following examples illustrate several configurations of the expandable member:

Variable Thickness Expandable Member

FIGS. 2 and 3 are drawings of the preferred embodiment of the invention. In this embodiment of expandable member 29, the walls of the member are of a variable thickness. The member is made from a balloon-like material that can be continuously and repeatedly expanded and contracted. The pressurized, expanded balloon should conform to the inside of the aorta, occluding the aorta upstream from the aortic arch arteries.

At the first edge of the expandable member, the edge closest to the opening 31, the walls 107 are their thickest, while the walls thin moving distally towards the back 57 of the member. In the collapsed position 101 shown in FIG. 2, the expandable member is drawn around the distal end 53 of the flexible tube, the pressurizing gas having been drawn from the member.

The thinnest section of the expandable member requires the least amount of pressure within the expandable member to inflate to a primary volume. This allows this section of the expandable member to expand first and to the greatest extent, thus placing the member in the blocking position. This is shown in dashed lines in FIG. 3 as position 103. The walls of the expandable member are thicker moving towards the portion of the expandable member facing the ostiums. As more gas pressure is applied through the lumen 27 to fill the member 29, the thicker portion will expand to a secondary volume, forming the blocking-pumping position 105 of the expandable member. This action has the effect of applying pressure to the blood within the ascending aorta region, and to the surge of blood pumped through opening 31. The net effect of the variable thickness wall of the expandable member 29 is a piston-like movement that forces blood to the coronary ostiums.

Two-Chambered Expandable Member

In this embodiment of the expandable member, member 29 has two working chambers: the first chamber and second chamber. The chambers are separated by a wall with at least one orifice to allow gas to flow between the two chambers. The member is made of suitable balloon-like material that can be continuously expanded and contracted, the expanded, pressurized balloon forming a piston-like shape that occludes the aorta. The proximal end 53 of the flexible tube is continuous to the opening at 31. The expandable member 29 is formed around the outside of the proximal end of the flexible tube. In the collapsed position, gas is drawn out of the expandable member 29 through lumen 27, thus drawing the member tightly around the distal end 53 of the flexible tube. Simultaneous to this, the pumping balloon is activated to its sucking position to enhance the blood-withdrawing effect. During diastole, the first chamber is pressurized to a primary volume. The pressurizing of the expandable member 29 to the primary volume creates the blocking position, blocking the ascending aorta 11 at 99, and forming an area within the ascending aorta between the expandable member 29 and the heart 35.

Next, the second chamber is pressurized to expand distally from the flexible tube towards the heart to a secondary volume, thus forming the blocking-pumping position of the expandable member. Simultaneous to this expansion, the pumping balloon 23 forces blood through flexible tube 25 and out of opening 31. The first and second chambers communicate through at least one orifice in the wall separating the chambers. The size of the opening is chosen to allow pressure to build up in the first chamber, followed by pressure building up in the second chamber. The net effect of the dual chamber expansion is to create a piston-like action, pushing blood in the direction of and into the coronary ostiums 33.

Advantages

There are several advantages of this invention over prior intra-aortic devices. Specifically improved coronary flow. This is highly desirable in emergency situations where time is of the essence in treating the patient and direct treatment of the heart is critical. Further, the expertise required to use most catheter devices is such that most emergency personnel could operate the device. This is also an advantage since emergency personnel are most often the first to aid heart attack patients.

This device has the advantage of combining the aortic arch blocking ability of some devices, while incorporating the oxygenated blood surge advantage of other intra-aortic devices. The cooperative effect of this dual function it to provide greater blood supply to both coronary arteries simultaneously, and ultimately the myocardium.

Also, this device supplies oxygenated blood to both of the coronary arteries at the same time. This is an advantage because locating the specific artery that is occluded is time consuming and requires expensive equipment. The present device and method does not require pre-screening for a specific coronary artery. Further, given the difficulty of actually placing an intra-aortic device within the ostium of a coronary artery, this device is much quicker and simpler to use than many prior art devices.

The device of the invention is useful as a coronary circulation assist device in cases of post-surgical damage to the cardiac tissue where the heart vessels are not necessarily occluded and a portion of the heart wall remains healthy. The device causes less mechanical damage to the blood than heart lung machines. The device can be used to the exclusion of an external blood supply. Thus, the need for anti-coagulant medications is greatly reduced when using the present invention. Further, the pressure sensing port and opening in the expandable member provide a convenient means for the administration of therapeutic drugs in the immediate region of the coronary circulation.

While the invention has been shown in the figures in only one of its forms, it is not thus limited but is susceptible to various changes and modifications without departing from the spirit thereof.

What is claimed is:

1. A device for assisting coronary blood circulation and cardiac contractile function when placed in the aorta of a patient, the aorta having an ascending portion and an inside wall, the device comprising:

a blood flow control means that alternately increases and decreases the blood pressure within an ascending aorta of a patient in synchrony with heart function;

an expandable member coupled to the blood flow control means;

a flexible tube having an internal bore, a proximal end and a distal end, the distal end being associated with the blood flow control means and the proximal end being associated with the expandable member which is actuable between a collapsed position, a blocking position and a blocking-pumping position;

the expandable member being positionable at a selected location in the ascending aorta and being inflatable in successive stages to the blocking and blocking-pumping positions, respectively, both positions fitting the expandable member against the inside wall of the aorta; and the expandable member in the blocking-pumping position extending distally to expand within the aorta, increasing the blood pressure upstream from the expandable member to force blood into the coronary arteries.

2. The device of claim 1, wherein the flexible tube has a lumen that is operatively coupled to the expandable member to supply gas for increasing and decreasing the pressure within the expandable member.

3. The device of claim 1, wherein the inflation of the expandable member is achieved by alternately filling and evacuating a gas through a lumen coupled to the expandable member.

4. The device of claim 1, wherein the expandable member is inflated to a primary volume in the blocking position, and a secondary volume in the blocking-pumping position, the secondary volume being greater than the primary volume.

5. The device of claim 1, wherein the expandable member is a variable thickness balloon.

6. The device of claim 1, wherein the expandable member comprises a first chamber and a second chamber, the second chamber located proximally from the first chamber, the chambers being separated by a wall with at least one orifice that allows expansion or contraction of the first chamber affects the expansion or contraction of the second chamber.

7. The device of claim 1, wherein a means is provided for measuring the blood pressure within the aorta.

8. The device of claim 1, wherein the blood flow control means is a pumping balloon located within the aorta of the patient.

9. The device of claim 8, wherein the pumping balloon is located within an inside chamber of a catheter body, the catheter body coupled to the distal end of the flexible tube.

10. A method for assisting coronary blood circulation and cardiac contractile function comprising:

providing a blood flow control means coupled to an expandable member;

providing a flexible tube having a proximal end and a distal end, the distal end being associated with the blood flow control means and the proximal end being associated with an expandable member which is coupled to a pressurization lumen;

placing the flexible tube, blood flow control means, and expandable member within the aorta of a patient, the expandable member being placed just above the coronary ostiums within the ascending aorta and the blood flow control means downstream from the expandable member; and supplying oxygenated blood to the coronary arteries by the simultaneous pressurization of the expandable member and activation of the blood flow control means to supply a surge of oxygenated blood to the ascending aorta.

11. A method for assisting coronary blood circulation and cardiac contractile function comprising:

providing a blood flow control means that alternately increases and decreases the blood pressure within an aorta in synchrony with heart function;

providing an expandable member coupled to the blood flow control means;

providing a flexible tube having an internal bore, a proximal end and a distal end, the distal end being associated with the blood flow control means and the proximal end being associated with an expandable member which is actuable between a collapsed position, a blocking position and a blocking-pumping position;

placing the flexible tube, expandable member, and blood flow control means within the aorta of the patient;

positioning the expandable member at a selected location within the ascending portion of the aorta of the patient;

pressurizing the expandable member to the blocking position during diastole to block the flow of blood to the aortic arch arteries and descending aorta; and pressurizing the expandable member to the blocking-pumping position to extend the member towards the heart in a piston-like action, increasing the blood pressure upstream from the expandable member to force blood into the coronary arteries during diastole.

12. The method of claim 11, providing oxygenated blood to the coronary arteries by a surge of blood through the internal bore of the flexible tube simultaneous to the expandable member being in the blocking-pumping position, the surge of blood increasing blood pressure within the aorta.

13. The method of claim 11, deflating the expandable member to the collapsed position during systole in synchrony with a decrease in pressure provided by the blood flow control means.

14. The method of claim 11, wherein the expandable member is filled to a primary volume in the blocking position, and a secondary volume in the blocking-pumping position, the secondary volume being greater than the primary volume.

15. The method of claim 11, wherein the flexible tube has an outside lumen layer that is operatively coupled to the expandable member as a pathway for gas, the gas increasing and decreasing the pressure within the expandable member, the lumen also being coupled to a gas control apparatus.

16. The method of claim 11, wherein the blood flow control means is a pumping balloon.

17. The method of claim 16, wherein the pumping balloon is located within an inside chamber of a catheter body, the catheter body coupled to the distal end of the flexible tube.

18. The method of claim 11, wherein a pressure sensor port is provided for allowing measurement of the blood pressure within the aorta.

19. The method of claim 11, wherein the expandable member forms a closed volume within the ascending aorta when in the blocking and blocking-pumping position.

* * * * *